United States Patent [19]

Fang et al.

[11] Patent Number: 5,811,277
[45] Date of Patent: Sep. 22, 1998

[54] METHOD FOR RECOVERY AND PURIFICATION OF ISOAMYLASE BY ADSORPTION ON RAW STARCH

[75] Inventors: Tsuei Yun Fang; Long Liu Lin; Wen Hwei Hsu, all of Hsinchu, Taiwan

[73] Assignee: Food Industry Research and Development Institute, China

[21] Appl. No.: 391,769

[22] Filed: Feb. 21, 1995

[51] Int. Cl.⁶ .............................. C12N 9/44; C12N 9/24
[52] U.S. Cl. ................... 435/210; 435/200; 210/660
[58] Field of Search ........................ 435/210, 200, 435/814, 815; 210/660

[56] References Cited

U.S. PATENT DOCUMENTS

| | | | |
|---|---|---|---|
| 3,560,345 | 2/1971 | Yokobayashi et al. | 435/210 |
| 4,058,631 | 11/1977 | Roan | 426/52 |
| 4,971,906 | 11/1990 | Melasniemi et al. | 435/98 |
| 5,204,254 | 4/1993 | Schmid et al. | 435/202 |
| 5,445,950 | 8/1995 | Kobayashi et al. | 435/99 |

OTHER PUBLICATIONS

Leloup et al., "α–Amylase Adsorption on Starch Crystallites." *Biotechnology and Bioengineer* 38:127–134, Jun. 1991.

Medda et al., "Raw Starch Adsorption and Elution Behaviour of Glycoamylase I of Black Aspergillus." *J. Ferment. Technol.,* 60(3):261–264, Jun. 1982.

Dalmia and Nikolov, "Characterization of Glucoamylase Adsorption to Raw Starch." *Enzyme Microb. Technol.,* 13:982–990, Dec. 1991.

Fang et al., "Recovery of Isomylase from *Pseudomonas amyloderamosa* by Adsorption–Elution on Raw Starch." *Enzyme Microb. Technol.,* 16:247–252, Mar. 1994.

Saha et al., "Raw Starch Adsorption–Desorption Purification of a Thermostable β–Amylase from *Clostridium thermosulfurogenes.*" *Analytical Biochemistry* 175:569–572, Dec. 1988.

*Primary Examiner*—Leon B. Lankford, Jr.
*Attorney, Agent, or Firm*—Scully, Scott, Murphy & Presser

[57] ABSTRACT

The present invention relates to a method for recovery and purification of isoamylase by raw starch adsorption method. Various raw starches are used to recover the isoamylase produced by a bacterium such as *Pseudomonas amyloderamosa*. The method comprises using raw starch to adsorb isoamylase under conditions suitable for such adsorption and isolating the adsorbed enzyme. The isoamylase adsorption rate varied with the species of raw starch. Additionally, raw starch can be recycled.

1 Claim, 2 Drawing Sheets

METHOD FOR RECOVERY AND
PURIFICATION OF ISOAMYLASE BY
ADSORPTION ON RAW STARCH

BACKGROUND OF INVENTION

Isoamylase (EC 3.2.1.68, glycogen 6-hydrolase) catalyzes the hydrolysis of the alpha-1,6 linkage of amylopectin and glycogen. The enzyme can be used in industrial production of high-maltose syrup, high-fructose syrup and Amylose. If starch is hydrolyzed by alpha-amylase and beta-amylase together with isoamylase, a product containing 95%–99% maltose can be generated. Chemical reduction of maltose produces maltitol. Maltitol is a sweetener with low caloric content and can be used in candy and bakery industries to make improvement in quality.

Many microorganisms produce isoamylase (Harada, T. Biotechnol. Genet. Eng. Rev. 1984, 1, 39). Among such microorganisms, *Pseudomonas amyloderamosa* has the highest producing capability (Harada, T., K. Yokobayashi, and A. Misaki. Appl. Microbiol. 1968, 16, 1439). Normally, the method for purification of isoamylase is varied with the source of the enzyme (Chang, S. M. and T. C. Chang. J. Chinese Agric. Chem. Soc. 1986, 24, 265; Swinton, S. J., and L. F. T. Woods. Food Biotechnol. 1989, 3, 197; Yokobayashi, K., A. Misaki, and T. Harada. Biochim. Biophys. Acta 1970, 212, 458; Kitagawa, H., A. Amemura, and T. Harada. Agric. Biol. Chem. 1975, 39, 989). Generally, the techniques used in purification include ionic exchange, molecular sieve and separation based on isoelectric point. A number of steps are required to obtain substantially pure enzyme when the above mentioned techniques are used. Therefore, it is economically necessary to develop an easier method for recovery of enzyme.

In view of the research reports, many amylolytic enzymes including glucoamylase, alphaamylase and beta-amylase have the characteristic of being adsorbed by raw starch. The mechanism is similar to the high-specificity affinity reaction between antigen and antibody. However, said adsorption-elution experiment was performed on purified enzymes. Up to date, the isolation and recovery of isoamylase using raw starch have never been reported.

DETAILED DESCRIPTION OF THE INVENTION

Figure 1:
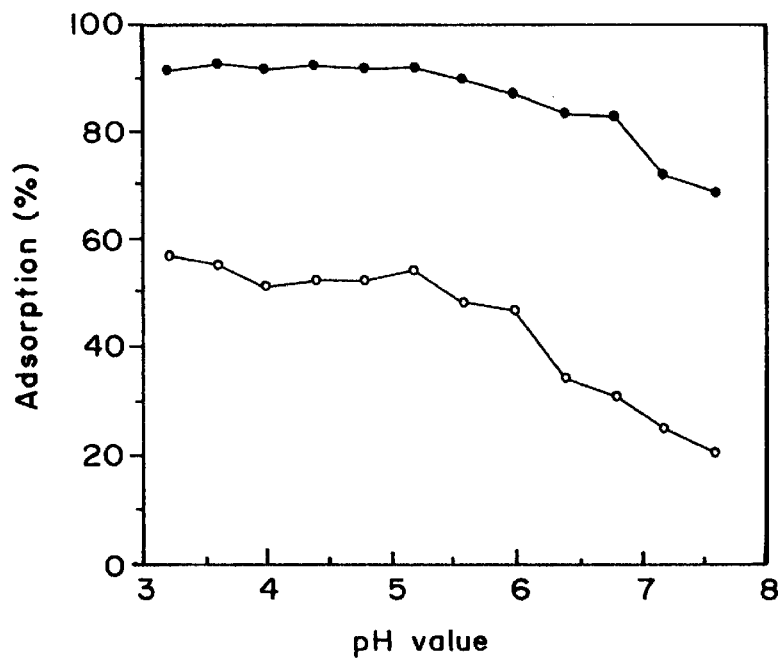
FIG. 1 shows the effect of pH on the adsorption of isoamylase onto raw starch. 100 mg raw starch was suspended in 5 ml crude enzyme solution (740 U/ml), adjusted to the indicated pH and kept at 4° C. for 1 hour. ●:corn starch, o:potato starch.

The present invention provides a method for recovery and purification of isoamylase, said method comprising: using raw starch to adsorb isoamylase in the fermentation broth of an isoamylas-producing bacterium.

Fermentation broth of any isoamylase-producing bacterium is useful in the present invention. The bacteria useful in the present invention only produce isoamylase but no other protein adsorbable by raw starch. Among such bacteria, *Pseudomonas amyloderamosa* is the most preferred.

The raw starch useful in the present invention include corn starch, rice starch, potato starch, or wheat starch, for example, that available from Sigma Chemical Co. (USA) and sweet potato starch, for example, that available from Wako Pure Chemical Co. (Japan). The condition for isoamylase adsorption onto raw starch is preferably acidic, for example, pH 2–7 and most preferrably pH 3.5–5.2. The temperature is preferably 0°–50° C. and more preferably below 10° C. Generally known methods for isolation of isoamylase adsorbed onto raw starch such as column separation or elution are useful in the present invention. Elution method is preferred, for example, using buffer solution containing saccharide as eluant. The saccharide is preferably of low molecular weight such as soluble starch, amylose, dextran and maltose wherein maltose is the most preferred. There follows a detailed description of certain preferred embodiments of the present invention, but these are intended to be illustrative only, and not in any way a limitation of the present invention.

EXAMPLE 1

Preparation of Enzyme Solution

*Pseudomonas amyloderamosa* WU 2130 used in this study is an isoamylase-hyperproducing mutant derived from *P. amyloderamosa* JD210 deposited in the Culture Collection and Research Center, Food Industry Research and Development Institute (Hsinchu, Taiwan). The seed medium (SM) is composed of (w/v) 1.0% maltose, 0.2% peptone, 0.1%($NH_4$)$_2$$HPO_4$, 0.05% $MgSO_4$.7$H_2O$ (pH 5.0); production medium (PM) is composed of (w/v) 2.0% maltose, 0.5% proteimax (Sanbra Co., Brazil), 0.3% $KH_2PO_4$, 0.05% $MgSO_4$.7$H_2O$ (pH 5.0). 0.5 ml bacterial cells stored in glycerol was used to inoculate a Hinton flask containing 10 ml SM. Incubation was at 30° C. on a rotary shaker at 150 rpm for 24 hours to activate bacterial cells. 5 ml culture broth was used to inoculate 100 ml SM and was incubated on a rotary shaker under the same condition for 16 to 20 hours to generate seed culture. 20 ml seed culture was used to inoculate 400 ml PM. Incubation was at 30° C. on a rotary shaker at 150 rpm for 2 days. The culture broth was collected and centrifuged in a frozen centrifuge (9000×g) for 40 minutes. The supernatant was used as crude enzyme solution. Enzyme activity was determined according to the method described in Harada, T., K. Yokobayashi, and A. Misaki. Appl. Microbiol. 1968, 16, 1439.

EXAMPLE 2

Recovery and Purification of Isoamylase by Using Raw Starch

1. The Effect of pH on the Adsorption of Isoamylase 100 mg raw starch was added to 5 ml crude enzyme solutions of different pH (1N HCl and 1N NaOH were used to adjust the solution to a desired pH). The solution was vigorously shook, incubated at 4° C. for 1 hour, centrifuged (12,000×g) for 1 minute and the enzyme activity remaining in the supernatant was then determined. The control group was operated similarly except that no raw starch was added.

$$\text{Enzyme adsorption (\%)} = \frac{\text{Enzyme activity of control group} - \text{Enzyme activity of supernatant}}{\text{Enzyme activity of control group}} \times 100$$

As shown in FIG. 1, optimum adsorption to corn starch or potato starch occurred in a broad pH range of 3.2–5.2. At any pH, enzyme adsorption onto corn starch was higher than that onto potato starch.

2. The Effect of Temperature on the Adsorption of Isoamylase 100 mg raw starch was added to 5 ml crude enzyme solution (pH 5.2). The solution was vigorously shook, incubated in a water bath of indicated temperature for 1 hour, centrifuged (12,000×g) for 1 minute and the enzyme activity remaining in the supernatant was then determined.

Figure 2:
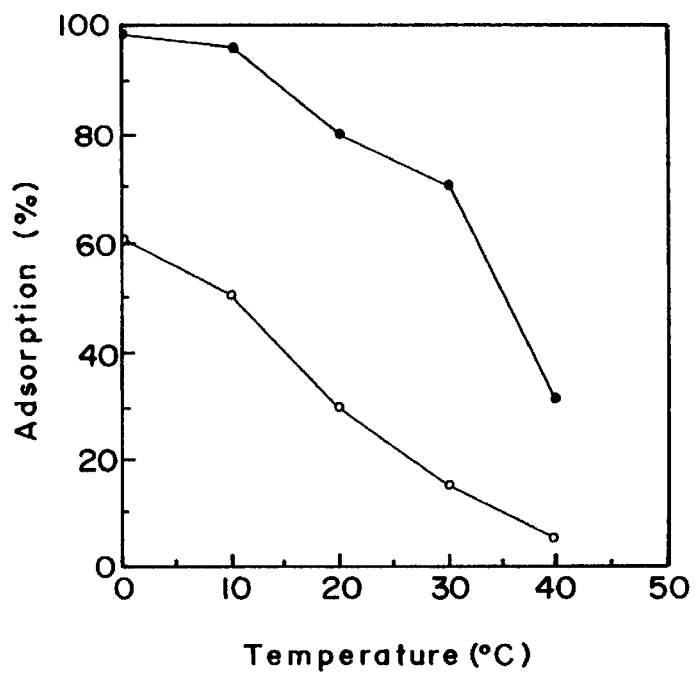
FIG. 2 shows the effect of temperature on the adsorption of isoamylase onto raw starch. 100 mg raw starch was suspended in 5 ml crude enzyme solution, adjusted to pH 5.2 and kept at the indicated temperature for 1 hour. ●:corn starch, o:potato starch.

Adsorption reaction was conducted at various temperatures. As shown in FIG. 2, the lower the temperature, the higher the adsorption. Adsorption to corn starch and potato starch respectively decreased 67% and 55% when the temperature was raised from 0° C. to 40° C. At any temperature, adsorption onto corn starch was higher than those onto other starches.

3. Elution of Isoamylase

Adsorption

One gram of raw starch was added to suitable amount of crude enzyme solution (pH 5.2) with agitation for 1 hour followed by standing for 3 hours at 4° C. Most of the supernatant was removed by vacuum pump and the residue was centrifuged (12,000×g) to remove the remaining supernatant. The enzyme activity of the original crude enzyme solution and that of the supernatant were determined. The enzyme activity adsorbed onto raw starch was defined as [the activity of the original crude enzyme solution—the activity of the supernatant].

Washing

The starch pellet with adsorbed enzyme was washed in 50 ml cold acetate buffer (0.05M, pH5.2), centrifuged and decanted of supernatant for three times.

Elution

The sample was suspended in 20 ml eluant buffer solution at 40° C., stirred for 1 hour to elute the enzyme, and centrifuged. The supernatant was collected and the enzyme activity in the supernatant was assayed. The eluted isoamylase activity was compared with the adsorbed enzyme activity to calculate the elution percentage.

$$\text{Elution percentage (\%)} = \frac{\text{Eluted isoamylase activity}}{\text{Adsorbed isoamylase activity}} \times 100$$

The result showed that acetate buffer containing 10% maltose gave an elution percentage of higher than 56%. The isoamylase adsorption capability of five starches including rice starch, corn starch, sweet potato starch, potato starch and wheat starch was tested. As shown in Table 1, corn starch and rice starch had highest isoamylase adsorption capability, wheat starch the second and potato starch the lowest. The elution percentage of isoamylase from various raw starches were in the range of 52–60%.

TABLE 1

The effect of various raw starches on the adsorption and elution of isoamylase[a]

| | Adsorbed Isoaylase | | Eluted Isoamylase | |
|---|---|---|---|---|
| Starch | Total Activity (U) | Adsorption (%) | Total Activity (U) | Elution (%) |
| Corn | 73,520 | 90.1 | 44,280 | 60.2 |
| Rice | 75,000 | 91.9 | 41,520 | 55.4 |
| Sweet potato | 58,740 | 72.0 | 31,600 | 53.8 |
| Potato | 42,000 | 51.5 | 21,960 | 52.3 |
| Wheat | 64,560 | 79.1 | 34,860 | 54.0 |

[a]One gram of raw starch was used to adsorb the isoamylase in 100 ml crude enzyme solution (816 U/ml). The eluant was 20 ml of 0.05M acetate buffer (pH 5.2) containing 10% maltose.

4. Determination of Purification Effect

Measurement of Protein

Protein was estimated by the Coomassie blue binding method (Scopes, R. K. In "Protein Purification: Principles and Practice" second edition, Springer-Verlag press, New York, Heidelberg, Berlin, London, Paris, Tokyo, P.306) with bovine serum albumin as standard. 1.5 ml sample was added to 1.5 ml Coomassie brilliant blue G-250 reagent (600 mg Coomassie brilliant blue in 1 liter 2% perchloric acid with insoluble materials removed) and incubated for 2 to 30 minutes. Adsorption at 595 nm was determined and compared with the standard curve.

Electrophoresis

Preparation of gel, electrophoresis and CBR staining were all performed according to the method described in the doctoral thesis by R. H. Chaung in Graduate School of Agricultural Chemistry, National Taiwan University.

Figure 4:
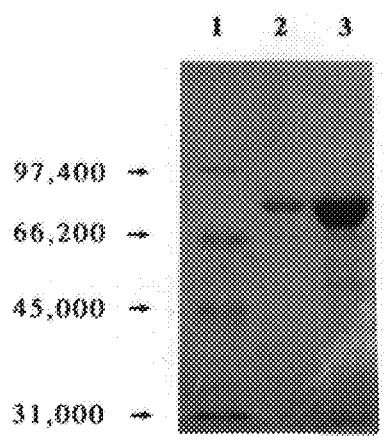
FIG. 4 shows CBR staining of purified isoamylase on SDS-PAGE. Lane 1 contained standard marker proteins. Lanes 2 and 3 contained the purified isoamylase of 0.44 and 4.4 ug, respectively.

Raw corn starch was used in the crude enzyme solution containing isoamylase to perform the adsorption and elution of isoamylase. The isoamylase purification effect is illustrated in Table 2. A 13.3-fold purification and 54% recovery were resulted. Purity was determined on SDS-PAGE. As shown in FIG. 4, the purified isoamylase had desirable purify and a molecular weight of 80,300.

TABLE 2

Purification of isoamylase by adsorption-elution on corn starch[a]

| | Activity (U/ml) | Total Activity (U) | Total Protein (mg) | Specific Activity (U/mg) | Purification fold | Recovery (%) |
|---|---|---|---|---|---|---|
| Crude enzyme solution | 805 | 80,500 | 14.74 | 5.461 | 1 | 100 |
| Adsorption-elution | 2,112 | 42,200 | 0.58 | 72.828 | 13.3 | 54 |

[a]One gram of raw starch was used to adsorb the isoamylase in 100 ml crude enzyme solution (816 U/ml). The eluant was 20 ml of 0.05M acetate buffer (pH 5.2) containing 10% maltose.

EXAMPLE 3

Repeated Use of Raw Starch

Figure 3:
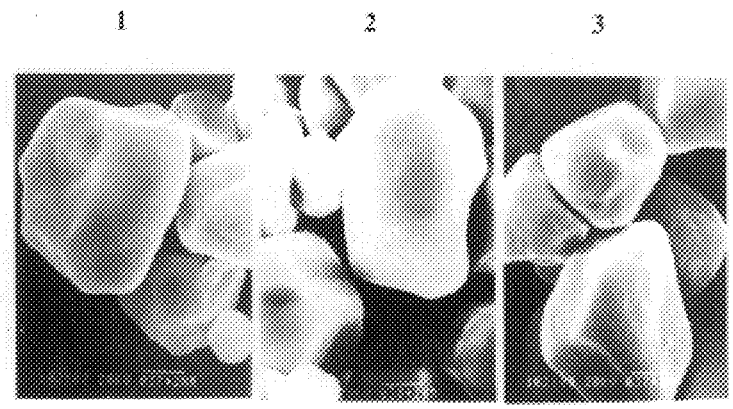
FIG. 3 shows scanning electron micrograph of raw corn starch before and after isoamylase was adsorbed and eluted. Lane 1, before adsorption; Lane 2, after adsorption; Lane 3 after elution.

Raw starch was repeatedly used in the adsorption-elution reaction. As shown in Table 3, no significant decrease in the adsorption and elution rates was detected. On the other hand, raw starch before and after isoamylase adsorption and elution was washed in cold distilled water and freeze-dried. The freeze-dried sample was coated with a thin layer of gold on an ion coater (Model IB-2, Hitachi Koki Ltd., Japan) and scanning electron microscopy was performed (Model S-450, Hitachi Koki Co., Japan). As shown in FIG. 3, isoamylase had no hydrolytic capacity on raw starch. The above results show that raw starch can be repeatedly used in isoamylase adsorption-elution reaction.

TABLE 3

Repeated use of raw corn starch for the adsorption and elution of isoamylase[a]

| Runs | Adsorption (%) | Elution (%) |
|------|----------------|-------------|
| 1st  | 90.7           | 57.8        |
| 2nd  | 89.3           | 57.5        |
| 3rd  | 90.2           | 55.4        |
| 4th  | 92.1           | 61.2        |

TABLE 3-continued

Repeated use of raw corn starch for the adsorption and elution of isoamylase[a]

| Runs | Adsorption (%) | Elution (%) |
|------|----------------|-------------|

[a]One gram of raw starch was used to adsorb the isoamylase in 100 ml crude enzyme solution (816 U/ml). The eluant was 20 ml of 0.05M acetate buffer (pH 5.2) containing 10% maltose.

We claim:

1. A method for recovery and purification of isoamylase comprising:

a. adding raw starch to the isoamylase in a fermentation broth of *Pseudomonas amyloderamosa* at a pH of 2–7 and a temperature of 0°–50° C. wherein said isoamylase is adsorbed onto said starch; and b. eluting the adsorbed enzyme with a buffer solution containing maltose.

* * * * *